United States Patent [19]

Buddenbaum et al.

[11] Patent Number: 4,684,643

[45] Date of Patent: Aug. 4, 1987

[54] PHARMACEUTICAL COMPOSITIONS FOR STORAGE IN PLASTIC CONTAINERS AND PROCESS THEREFOR

[75] Inventors: Harry C. Buddenbaum, Indianapolis; Robert L. Robison, Greenwood, both of Ind.

[73] Assignee: Eli Lilly and Company, Indianapolis, Ind.

[21] Appl. No.: 740,788

[22] Filed: Jun. 3, 1985

Related U.S. Application Data

[62] Division of Ser. No. 525,347, Aug. 22, 1983, Pat. No. 4,533,542.

[51] Int. Cl.$^4$ .............................................. A61J 3/02
[52] U.S. Cl. .................................... 514/204; 514/788; 424/114
[58] Field of Search .................. 424/31, 114; 514/204, 514/788

[56] References Cited

U.S. PATENT DOCUMENTS

| | | | |
|---|---|---|---|
| 2,745,785 | 5/1956 | Bruce et al. | 424/271 |
| 3,351,527 | 11/1967 | Apat et al. | 424/31 |
| 4,081,545 | 3/1978 | Clayton | 424/271 |
| 4,166,817 | 9/1979 | Ferres et al. | 424/271 |
| 4,421,760 | 12/1983 | Box | 424/114 |
| 4,427,690 | 1/1984 | Cole et al. | 424/267 |
| 4,447,422 | 5/1984 | Taylor et al. | 424/229 |

FOREIGN PATENT DOCUMENTS

| | | | |
|---|---|---|---|
| 154446 | 12/1953 | Australia | 424/271 |
| 571275 | 2/1959 | Canada | 424/271 |
| 49-54513 | 5/1974 | Japan | 424/271 |
| 655519 | 7/1951 | United Kingdom | 424/271 |
| 705343 | 3/1954 | United Kingdom | 424/271 |
| 816239 | 7/1959 | United Kingdom | 424/271 |

OTHER PUBLICATIONS

Trandafilova C.A. 79 #45671 (1973), 80 #19416p (1974), 80 #124703c (1974).
Kobayashi et al. C.A. 83 #48122g (1975).
Franz C.A. 92 #220701u (1980).
Sebgal C.A. 96 #129797(b) (1982).
Los C.A. 97 #78915z (1982).
Aguiar C.A. 97 #188287d (1982).
B. E. Ballard, "Prolonged-Action Pharmaceuticals", in Arthur Osol, editor, Remington's Pharmaceutical Science, 16th ed., Mack Publishing Co., Easton, PA, Ch. 91, pp. 1609-1613 (1980).
Y. J. Wang and R. R. Kowal, "Review of Excipients and pH's for Parenteral Products" etc., J. Parenteral Drug Ass'n., 34, pp. 452-463 (1980).

Primary Examiner—Shep K. Rose
Attorney, Agent, or Firm—Paul C. Steinhardt; Leroy Whitaker

[57] ABSTRACT

The instant invention is a pharmaceutical composition suitable for storage in plastic containers which comprises a pharmaceutical compound in powder form coated with a surfactant. A second aspect of the invention is a method for making the composition. This method encompasses applying a solution of a surfactant to the surface of a pharmaceutical compound in powder form and then drying the composition.

10 Claims, No Drawings

PHARMACEUTICAL COMPOSITIONS FOR STORAGE IN PLASTIC CONTAINERS AND PROCESS THEREFOR

This application is a division of application Ser. No. 525,347, filed Aug. 22, 1983, now U.S. Pat. No. 4,533,542.

BACKGROUND OF THE INVENTION

The instant invention employs surfactants to enhance the pharmaceutical elegance of reconstituted solutions of pharmaceutical powders stored in plastic containers. The enhancement afforded by the instant process and composition is achieved whether the powder is to be reconstituted in the plastic container or the powder is to be removed from the plastic container then reconstituted. A preferred embodiment of the invention encompasses parenteral pharmaceutical compounds in powder form stored in plastic containers.

Additives, impurities, and monomers and oligomers will often migrate from the plastic container onto the pharmaceutical powder stored therein. Examples of substances that can migrate from the plastic onto the powder include mold release, anit-slip, anti-static and anti-oxidant agents, plasticizers, coloring agents, primers, heat-sealable coatings, machineability coatings, and barrier coatings, etc.

The migrating components form an emulsion that appears as "haze" when the pharmaceutical powder is reconstituted. The haze may be visible while the solution is in the plastic container and is visible when the reconstituted solution is placed in a glass container for inspection. The presence of haze may cause the observer to reject the solution as unsuitable for administration even though the solution is not necessarily harmful to the patient.

The packaging and storage of pharmaceutical powders in plastic containers, especially pharmaceutical powders that are to be reconstituted for parenteral administration, is known. For instance, two antibiotics, cefazolin sodium and cephalothin sodium, are stored in reconstitutible powder form in flexible plastic bags.

The use of surfactants to solubilize pharmaceutical compounds has been described in articles such as *J. Pharm, Sci.*, 54:9, 1229 (1965). However, the above reference does not teach a method to reduce or eliminate the haze caused by the migration of components and contaminants of the plastic container onto the pharmaceutical compound in powder form.

SUMMARY

The object of the instant invention is to substantially reduce or eliminate the haze observed in reconstituted solutions of pharmaceutical compounds stored in plastic containers and to thus improve the pharmaceutical elegance of the product. This object is achieved by coating the pharmaceutical powder with a surfactant before placing the pharmaceutical powder in the plastic container.

DETAILED DESCRIPTION

This invention comprises both a pharmaceutical composition suitable for storing in and dispensing from a plastic container and a method for substantially reducing or eliminating the formation of haze in reconstituted pharmaceutical compositions stored in plastic containers.

Specifically, the pharmaceutical composition aspect of the instant invention is a pharmaceutical compound in powder form wherein a surfactant has been applied to the surface.

The plastic container used with the composition of this invention may be a flexible container such as a pouch or a bottle, or a rigid container such as a rigid bottle or a vial. All or part of the container may be plastic. The plastic container may have an opening or port that is made from material other than plastic. The types of plastics commonly used for fashioning such plastic containers are pharmaceutically acceptable thermoplastic polymers, either pure or compounded. More specifically, plastics such as high density polyethylene, medium density polyethylene, low density polyethylene, polypropylene, polymethylene, flexible polyvinyl chloride, rigid polyvinyl chloride, polycarbonate, polyamide (nylon), ionomers, polystyrene, polyallomers, polytetrafluorethylene, polymonotrifluorethylene, polyacrylates and acrylic multipolymers (nitryl polymers) are acceptable materials. Also, compound polymeric plastics such as poly(ethylene-vinyl acetate) and poly(styrene-acrylonitrile) are examples of acceptable materials from which to fashion the plastic containers. Plastic containers made from two or more layers of different or the same plastic films are acceptable. The layered plastic material for these plastic containers can be made by coextrusion, extrusion lamination, or adhesive lamination. All that is required of the layered plastic is that the innermost layer of plastic film, i.e., the layer that the pharmaceutical powder will be in contact with, be pharmaceutically acceptable. Examples of acceptable coextruded layered plastics include nylon/-polyethylene, nylon/ethylene vinyl acetate copolymer and polyester/polyethylene. A pharmaceutical composition of this invention is especially suitable for use in the flexible plastic pouches that have enjoyed increased use in recent times. A pharmaceutical composition of this invention is especially suitable for use in plastic containers of medium density polyethylene, or a layer of plastic material in which medium density polyethylene is the layer with which the powdered pharmaceutical composition will come in contact. Even more desirable is a plastic container made from pure medium density polyethylene, in other words, a medium density polyethylene where no additives are present in the film.

Of course, as above, it is preferred to use the medium density polyethylene as the innermost layer of a container made from a multi-layer plastic container. More specifically, it is preferred that a plastic material composed of an outer layer of polyester and an inner layer of pure medium density polyethylene be used for the plastic container. Two such multi-layer plastic materials are available commercially by the Minnesota Mining and Manufacturing Company under the trademark SCOTCHPAK. SCOTCHPAK #8 is a plastic material composed of a 0.5 mil polyester outer layer on a 1.5 mil medium density polyethylene inner layer. The second is SCOTCHPAK #48, which is a 0.5 mil polyester film on an inner layer of 4 mil medium density polyethylene.

Finally, it is most preferred that either of the above two SCOTCHPAK plastic materials are fashioned into a flexible package with a port-forming member at one end, as described by John W. Clarke and Dale C. Harris, in U.S. application Ser. No. 332,495, filed Dec. 21, 1981 and herein incorporated by reference.

In the above description of the instant pharmaceutical composition, the term "pharmaceutical compound" can be a prescription or non-prescription compound for use in warm-blooded animals. The pharmaceutical compound can be such that it is administered orally, topically, parenterally, or for ophthalmic use. Specifically, by "parenteral use" we mean methods of administration by injection such as subcutaneous, intramuscular, intravenous, intrasternal, intraperitoneal, intrathecal and the like.

By the term "pharmaceutical compound", we mean pharmaceuticals that are used as anesthetics, hypnotics, sedatives, muscle relaxants, analgesics, antipyretics, anti-inflammatory agents, central nervous system stimulants, anticholinesterase agents, catecholamines, sympathominetic amines that are non-catecholamines, antimuscarinic agents, (alpha)-andronergic blocking agents, (beta)-andronergic blocking agents, andronergic neuron blocking agents, ganglionic stimulating and blocking agents, neuromuscular blocking agents, autocoids (e.g., histamines, antihistamines, angiotensin, prostaglandin, plasma kinins), cardiovascular drugs (e.g., digitalis, antiarryhythmics, antihyertensives, vasodilators), oxytocics, digestants, urinary tract antiseptics, anthelmintics, antimalarials, drugs for treating amebiasis, antiprotoozals, antimicrobials (e.g., antibaterials, antifungals, and antivirals), anti-neoplastic agents (e.g., alkylating agents, antimetabolites, vinca alkaloids, antibiotics, L-asparaginases, and radioactive isotopes), iron and iron salts, folic acid, heparin, hormones, hormone antagonists, various vitamins, electrolytes, amino acids, minerals and other nutritional supplements. All that is further required of the above listing of classes of pharmaceutical compounds is that they be in powder form and, further, that the powders are to be reconstituted before administering.

By the term "powder", we mean any particular solid form, such as crystals, an amorphous solid, a spray-dried or a freeze-dried solid (lyophilate).

By the terms "reconstitute", "reconstitutible", and "reconstitution", we mean a process where water or an aqueous vehicle is added to the pharmaceutical compound in powder form to prepare a product suitable for administration, whether orally, topically, by injection, or the like. For example, in the case of injectable pharmaceuticals, the reconstituing vehicle is Sterile Water for Injection, U.S.P., Sterile Dextrose Injection, U.S.P., or Sterile Sodium Chloride Injection, U.S.P. Other suitable aqueous reconstituting vehicles known in the art are also acceptable for the purposes of the instant invention.

The instant pharmaceutical composition may be reconstituted either in the plastic container or the powder may be removed from the plastic container and reconstituted in any other container.

The preferred pharmaceutical compounds for use in the compositions of the instant invention are those compounds which are to be administered by injection. The more preferred pharmaceutical compounds are those antimicrobials and antineoplastic agents that are to be administered by injection. Examples of the preferred parenteral antimicrobials to be administered by injection include the injectable form of antibiotics such as cephalothin, cefazolin, moxalactam, cefoperazone, cefamandole, cefotaxime, cephradine, cephrapirin, cefoxitin, ceftazidime, penicillin G, methicillin, oxacillin, nafcillin, ampicillin, carbenicillin, ticaricillin, piperacillin, mezlocillin, capreomycin, streptomycin, tobramycin, amikacin, kanamycin, neomycin, chlorotetracycline, oxytetracycline, tetracycline, doxycycline, minocycline, chloramphenicol, erythromycin, clindamycin, spectinomycin, polymyxin B, colistimethate and vancomycin.

Preferred antifungals under the pereferred antimicrobials include the injectable forms amphotericin B and hydroxystilbamidine.

Preferred antivirals indlude the injectable forms of vidarabine.

Preferred anti-neoplastic agents include the injectable forms of vinblastine, vincristine, dactinomycin, doxorubicin, bleomycin, mithramycin, mitomycin and cisplatin.

More preferred pharmaceutical compounds for the instant invention include the above-listed antibiotics to be administered by injection.

More preferred of the above parenteral antibiotics are the injectable forms of ampicillin, cephalothin, cefazolin, moxalactam, cefamandole, tobramycin, ceftazidime and vancomycin. Especially preferred compositions comprise as the active ingredient the injectable forms of cefazolin and cefamandole.

The most preferred pharmaceutical compound for the instant composition is the injectable forms of cefazolin.

The term "injectable form(s)" means the various neutral and salt forms and the various solvates thereof approved by the U.S. Food and Drug Administration as acceptable for administration by injection. The term also encompasses the presence of approved buffering agents in conjunction with the pharmaceutical compound. In addition, the term includes the immediate precursors to the approved forms for administration. Such precursors are often the neutral form of the compounds which is then packaged with a weak acid or base. The weak acid or base will form the salt of the compound upon reconstitution. For example, cefamandole nafate is packaged with sodium carbonate. Upon reconstitution, the sodium carbonate reacts with the nafate form to give cefamandole sodium, the approved form for injection.

The term "surfactant" denotes an amphiphilic molecule that has both a hydrophilic and hydrophobic center. Also, the surfactant must not itself cause haze in the reconstituted solution and furthermore be acceptable for pharmaceutical use. Finally, the concentration of the surfactants should be within a medically acceptable range. In other word, surfactants that possess pharmaceutical properties should be present in such concentrations so that these properties do not manifest themselves in the animal or person receiving the composition.

Examples of classes of molecules encompassed by the instant term "surfactants" include low molecular weight carboxylic acid salts. Such salts include the alkali metal salts of $C_3$ to $C_{18}$ carboxylic acids, e.g. the alkali metal salts of propionic, butyric, lactic, caproic, caprylic, pelargonic, capric, lauric, myristic, palmitic, stearic, palmitoleic, oleic, elaidic, vaccenic, linoleic, α-linolenic, γ-linolenic, eleostearic, benzoic, naphanoic, phenylacetic, ascorbic, sorbic, citric, malic, tartaric and like acids.

The term "surfactants" includes the polyols, such as sorbitol and mannitol, and the glycols, such as polypropylene glycol.

Also, the instant term "surfactants" encompasses those molecules referred to in the art as surfactants, i.e., organic molecules with a molecular weight of 200 or greater possessing both a hydrophilic and a hydrophobic group. These are usually long chain organic compounds.

The preferred surfactants of the instant invention are those molecules that are known in the art as surfactants. Suitable molecules can be found within all four classes of compounds within the conventional surfactant group. For example, acceptable anionic surfactants include surfactants such as carboxylic acids (e.g., lactylates), sulfuric acid esters (e.g., sulfated monoglycerides and alkyl sulfates), substituted alkylamides (e.g., sarcosinates) and hemiesters (e.g., sulfosuccinates). Acceptable cationic surfactants include the quaternaries (e.g., benzalkonium chloride). Acceptable amphoteric surfactants include the ammonium carboxylates (e.g., N-alkylamino acids). Acceptable nonionic surfactants include polyalkoxy ethers (e.g., polyoxyethylene alkyl/aryl ethers), polyoxyethylene polyoxypropylene blocked polymers, polyalkoxy esters (e.g., polyoxyyethylene fatty acid esters, and polyoxyethylene sorbitan acid esters) and fatty acid esters of polyhydric alcohols (e.g., glyceryl esters and sorbitan esters).

The preferred conventional surfactants for the instant invention have an HLB (hydrophile-lipophile balance) value of about seven or greater.

The preferred surfactants for the instant invention that have an HLB value of approximately 7 or greater include polyethylene glycol (200) monooleate, sucrose dioleate, sorbitan monolaurate, polyoxyethylene (4) lauryl ether, polyoxyethylene (4) sorbitan monostearate, polyoxyethylene (6) ethyl ether, polyoxyethylene (20) sorbitan monooleate, poly(ethylene glycol)-30 caster oil, poly(ethylene glycol)-40 caster oil, poloxamer 188, polyoxyethylene (20) sorbitan tristearate, polyoxyethylene glycol (400) monooleate, polyoxyethylene glycol (400) monostearate, polyoxyethylene (9) nonyl phenol, polyoxyethylene glycol (400) monolaurate, polyoxyethylene (4) sorbitan monolaurate, polyoxyethylene (20) oleyl ether, polyoxyethylene (20) sorbitan monopalmitate, polyoxyethylene (20) cetyl ether, polyoxyethylene (40) stearate, sodium oleate, polyoxyethylene (100) stearate, and potassium oleate.

The more preferred surfactants for the instant invention are polyoxyethylene (20) sorbitan monooleate, poly(ethylene glycol)-40 castor oil and poloxamer 188. The most preferred surfactant for the instant invention is polyoxyethylene (20) sorbitan monooleate.

The amount of surfactant to be applied to the pharmaceutical compound should be in amounts sufficient to reduce the haze observed in a reconstituted solution of the pharmaceutical composition so that the reduction is detectable with the naked eye. A surfactant concentration sufficient to have this effect is between about 1 ppm to about 10,000 ppm of surfactant per amount of pharmaceutical compound present. A preferred concentration for the surfactant is in the range of approximately 10 ppm to about 5000 ppm of surfactant per pharmaceutical compound present. A more preferred range is between about 10 ppm to about 1000 ppm. The most preferred range for surfactant concentration is between about 100 ppm to about 1000 ppm.

The second aspect of this invention is a method for substantially reducing or eliminating the formation of haze in reconstituted pharmaceutical compositions stored in plastic containers. Specifically, the instant method comprises applying a solution of surfactant to the powder form of a pharmaceutical compound then drying the pharmaceutical composition. It is understood that the pharmaceutical compound should be substantially insoluble in the solvent of the surfactant solution. In the above description of the instant method, the terms "pharmaceutical compound", "plastic container", "surfactant", "parenterally", "injectable form(s)" "powder form", and "reconstituted" have the same meaning as discussed for the composition aspect of this invention. In the above description of the method of this invention, the term "haze" denotes the turbidity imparted to the reconstituted solution that can be seen by simple visual inspection and which is caused by the presence of lipophilic substances in the solution. The lipophilic substances in turn were present on the pharmaceutical powder before the powder was reconstituted.

As used to describe the instant method, the term "solvent" denotes an organic liquid in which the surfactant moiety is substantially soluble and which the pharmaceutical compound is substantially insoluble. In addition, the solvent must be pharmaceutically acceptable. Examples of such solvents include water, acetone, ethanol, chloroform, ether, ethyl acetate and isopropyl alcohol, or a mixture thereof. Isopropyl alcohol is a preferred solvent.

As used in the above description of the instant method, the term "drying" implies any method known in the pharmaceutical art to remove excess surfactant solution of the solvent. This includes removal by gravitational force (such as gravity or suction filtration) as well as evaporation. Evaporation may be carried out at room temperature or aided by the application of a vacuum and/or heat. Another suitable method is the spray drying technique. The preferred method of drying for the instant method is by evaporation, either at room temperature only or by the application of supplemental heat and vacuum.

By the term "coated" or "coating" we mean that part or all of the particulate matter of the pharmaceutical compound may be covered with a layer of the surfactant.

In addition, coated and uncoated particles may be blended together for the purposes of this invention, but it is preferred that substantially all the particles in the plastic container be coated for best results.

In carrying out the instant method, the pharmaceutical compound to be coated is weighed, and a sufficient amount of surfactant is dissolved or suspended in the solvent to coat that amount of compound within a specified concentration range. The concentration range for the surfactant should be between about 1 ppm to 10,000 ppm. A preferred surfactant concentration range is between about 10 ppm to 500 ppm, with a more preferred range being between about 10 ppm to 100 ppm. The most preferred concentration range is between about 100 ppm to about 1000 ppm.

The solution of the surfactant may then be applied to the surface of powder by spraying the powder in a rotating drum with the surfactant solution. The rotating drum may be a dryer-type drum which can be usd to evaporate the solvent after coating.

Alternatively, the pharmaceutical compound in powder form can be coated in this method by slurrying the powder in the surfactant solution and filtering and drying the powder. The fluidized bed technique is also an acceptable method for coating the powder with the surfactant.

In a preferred embodiment of the method, cefazolin sodium is placed in a suction filter and washed with a solution of polyoxyethylene (20) sorbitan monooleate in isopropyl alcohol. The excess solution is removed by suction on the filter and the coated powder is dried in a drum dryer under low heat and vacuum.

On a smaller scale, the coated powder can be dried with a rotary evaporator.

Those skilled in the pharmaceutical art will understand that, for parenteral compositions, stringent controls must be maintained during the instant method to insure the cleanliness and sterility of the pharmaceutical composition in the plastic container. As a minimum procedure, it is neceessary to clean and sterilize the plastic container, and to apply chemically pure surfactant in a reagent grade solvent to the powder in a clean, controlled environment. The pharmaceutical composition is then placed in the clean, sterilized plastic containers under aseptic conditions.

Furthermore, in handling parenteral pharmaceutical compositions of the instant invention, it is best to prepare a sterile pharmaceutical compound, then apply the surfactant solution to the pharmaceutical compounds under aseptic conditions.

The effect of the instant invention is to substantially reduce or eliminate the haze that often results in reconstituted solutions of pharmaceuticals in powder form stored in plastic containers. The instant invention enhances the pharmaceutical elegance of these reconstituted pharmaceutical solutions. The phenomenon of haze is visible to the naked eye and may cause the physician, pharmacist or nurse to discard the reconstituted solution.

A common situation where the haze in such a reconstituted solution will be observed occurs when the pharmacist inspects the solution immediately after he reconstitutes it. The pharmacist will often remove part or all of the solution from the plastic bag and place it in a clean glass bottle. The bottle is then examined under a good light, baffled against reflections into the examining pharmacist's eyes and viewed against a black and white background, after the contents have been set in motion with a swirling action.

One possible cause for the haze observed in a reconstituted solution (from a powder that has been stored in a plastic container) is the presence of lipophilic substances that were incorporated in the plastic. Such lipophilic substances include additives, monomers, oligomers and contaminants of the plastic. The presence of the lipophilic substances originating from the plastic is not harmful to the patient, however. The plastic material in contact with the pharmaceutical powder must have passed the biological tests required of plastics specified for parenteral containers set forth in *United States Pharmocopeia*, Twentieth Revision, pp. 951–953. Unfortunately, there is no easy way for the pharmacist to differentiate between the varying causes of the haze in the reconstituted solution. Hence, he may dispose of the solution because it is hazy, even when the haze-causing agent (e.g., lipophilic substances) presents no harm to the patient.

Applicants postulate that the mechanism by which the instant invention substantially reduces or eliminates the haze observed in reconstituted solutions of pharmaceutical powders is by preventing the migration of lipophilic substances onto the powder from the plastic. Applicants further postulate that this mechanism occurs because the coating of surfactant on the surface of the powder alters the lipophilic nature of the powder and hence reduces the amount of lipophilic substances that migrate from the plastic onto the powder when the two are in contact.

The above mechanism may be implied from the following experiments demonstrating the efficacy of the instant invention in substantially reducing or eliminating haze in reconstituted solutions of pharmaceutical powders. In one such experiment, a 2% solution of cefazolin sodium was made with either Water for Injection, U.S.P., Sterile (5%) Dextrose Injection, U.S.P. or Sodium Chloride Injection, U.S.P. Aliquots of each solution were placed in plastic bags fashtioned from a plastic laminate composed of a 0.5 mil outer layer of polyester and a 4.0 mil inner layer of pure medium-density polyethylene. The plastic bags had an opening port that was sealed with a rubber septum. Other aliquots of each solution were placed in clean glass bottles that had a rubber septum closure. The filled plastic bags and glass bottles were stored for 0, 24, 48 or 96 hours at either 5° C. or 25° C. An aliquot from 2 bags and 2 bottles at each time and temperature combination were analyzed for clarity with a nephelometer.

The results of this experiment are tabulated in Table 1. The storage temperatures are expressed in degrees centigrade. The numerical values reported are in units of nephelos. Note that the higher the nephelo value, the less clarity, and hence higher turbidity, of the solution being analyzed.

TABLE 1

| CLARITY OF (UNCOATED) CEFAZOLIN SODIUM SOLUTIONS | | | | | | | |
|---|---|---|---|---|---|---|---|
| Storage Time (Hours) | Storage Temp. | Water | | 5% Dextrose in Water | | Sodium Chloride | |
| | | Plastic | Glass | Plastic | Glass | Plastic | Glass |
| 0 | RT | 7,9 | 2,2 | 4,8 | 1,1 | 11,7 | 3,3 |
| 24 | 5 | 7,8 | 1,2 | 6,4 | 1,1 | 9,6 | 4,1 |
| 48 | 5 | 10,9 | 1,4 | 4,5 | 0,0 | 8,7 | 4,1 |
| 96 | 5 | 9,10 | 3,2 | 6,6 | 3,3 | 5,4 | 3,2 |
| 24 | 25 | 7,8 | 1,2 | 4,5 | 1,2 | 6,7 | 1,2 |

The data in the above table indicates that the amount of haze caused by the leaching of monomers and oligomers into the cefazolin sodium solutions is negligible. It is assumed that the turbidity of the solution is caused essentially by (lipophilic) monomers and oligomers from the polyethylene because the polyethylene layer is pure, i.e., free of additives. Furthermore, the difference of a few nephelos observed between the solutions stored in the plastic containers and the glass bottles is within the experimental error of the nephelometer instrument.

The conclusion to be drawn from the results in Table 1 is that any significant turbidity seen in reconstituted solutions stored in similar plastic bags must be due to the migration of monomers and oligomers onto the powder, and not due to leaching of the monomers and oligomers into the solution.

Evidence of such migration was found in the following experiment. Separate lots of cefazolin sodium powder were coated with three different concentrations of polyoxyethylene (20) sorbitan monooleate (PSMO). Portions of each of these coated lots were placed into plastic bags. Alsol, a number of plastic bags were filled with cefazolin sodium which was not coated with surfactant. The plastic bags were the same type of plastic bags used for the experiment summarized in Table 1 above. All filled plastic bags were then stored at room temperature for 151 days. At the end of this time, six bags at each concentration of PSMO were opened and the powder was empited from the bags into containers. A portion of the combined powder was chemically assayed for hydrocarbon concentration.

The weight of the samples assayed and the hydrocarbon concentration found are listed under the columns in Table 2 entitled "Powder".

Next, the walls of the above plastic containers were rinsed with water. The rinses were collected and combined, then a portion of the combination was chemically assayed for hydrocarbon concentration. The weight of the dried samples and the hydrocarbon concentration detected are listed under the columns entitled "Rinse".

Finally, the concentrations of hydrocarbons found for the "Powder" and "Rinse" samples were averaged in proportion to the weight of each portion to give the concentration value under the column entitled "Total".

The results from the above experiment are tabulated below in Table 2.

TABLE 2
HYDROCARBON ASSAY ON CEFAZOLIN SODIUM COATED WITH PSMO

| Surfactant Concentration (PPM) | Weight of Sample (g) | | | Hydrocarbon Conc. (PPM) | | |
|---|---|---|---|---|---|---|
| | Powder | Rinse | Total | Powder | Rinse | Total |
| 0 | 6.23 | 0.30 | 6.53 | 68 | 156 | 72 |
| 151 | 6.22 | 0.30 | 6.52 | 45 | 78 | 46 |
| 335 | 6.23 | 0.36 | 6.59 | 25 | 51 | 26 |
| 669 | 6.30 | 0.30 | 6.60 | 22 | 44 | 23 |

The results listed in the "Powder" column of the above Table indicates that hydrocarbon migration from the plastic bag to the powder is occurring. (The term "hydrocarbon" indicates the presence of monomers and oligomers from the polyethylene inner layer.) This conclusion is based on the observation that no solvent was ever in contact with both the powder and the plastic bag at the same time, precluding the possbility of the leaching of polyethylene monomers and oligomers into the reconstituted solution of pharmaceutical powder.

The second observation to be made from the above Table 2 is that an increase in the concentration of surfactant decreases the concentration of hydrocarbon detected. Therefore, the presence of the surfactant on the cefazolin sodium powder decreases the amount of migration of monomers and oligomers from the plastic bag onto the coated powder.

Further evidence of the prevention of migration of polyethylene monomers and oligomers from a plastic container to a pharmaceutical powder is presented by experiments summarized in Tables 3, 4 and 5 below. The procedure followed in these experiments entailed coating lots of cefazolin sodium powder with differing concentrations of polyoxyethylene (20) sorbitan monooleate (PSMO), poloxamer 188 (Pluronic ® F68, available from BASF Wyandotte Corp., Wyandotte, Michigan, 48192), and poly(ethylene glycol)-40 caster oil (Emulphor ® EL-719, availble from GAF Corp., 140 W. 51st Street, New York, N. Y. 10020) (Tables 3, 4 and 5, respectively). Portions of these lots were placed in the same type of plastic bag as the plastic bag of the experiments tabulated in Table 1 and 2. Plastic bags containing the coated powder were stored at either 25° C. ("RT") or 40° C. for the specified intervals of time. Also, cefazolin sodium that was not coated with any surfactant was stored under the same conditions as the surfactant-coated compound.

At each interval of time, two bags were reconstituted by the addition of water. Parts of the reconstituted solutions were then diluted with water at both 10% and 2% of original strength. Aliquots of both the 10% and 2% solutions were analyzed for clarity with a nephelometer. The nephelometer readings for both bags at each interval of time is reported in the Tables below.

The numerical values reported in Tables 3, 4 and 5 are in units of nephelos.

TABLE 3
CEFAZOLIN SODIUM COATED WITH PSMO

| | Stor-age Temp. | 10% Solutions Surfactant Conc. (PPM) | | | | 2% Solutions Surfactant Conc. (PPM) | | | |
|---|---|---|---|---|---|---|---|---|---|
| Days | | 0 | 1 | 10 | 100 | 0 | 1 | 10 | 100 |
| 0 | RT | 14,13 | 25,12 | 14,13 | 7,7 | 3,3 | 3,3 | 4,4 | 3,4 |
| 3 | 40 | 27,34 | 32,20 | 28,36 | 9,6 | 7,9 | 8,4 | 7,9 | 1,1 |
| 6 | 40 | 42,44 | 37,39 | 46,37 | 13,13 | 10,11 | 9,10 | 12,9 | 3,4 |
| 36 | 40 | 27,34 | 28,24 | 36,27 | 14,0 | 7,5 | 7,5 | 9,7 | 3,0 |
| 59 | RT | 36,50 | 41,42 | 44,43 | 11,11 | 10,13 | 11,11 | 11,11 | 3,3 |

TABLE 4
CEFAZOLIN SODIUM COATED WITH PLURONIC ® F-68

| | Stor-age Temp. | 10% Solutions Surfactant Conc. (PPM) | | | | 2% Solutions Surfactant Conc. (PPM) | | | |
|---|---|---|---|---|---|---|---|---|---|
| Days | | 0 | 1 | 10 | 100 | 0 | 1 | 10 | 100 |
| 0 | RT | 16,15 | 29,32 | 11,10 | 9,10 | 5,3 | 12,9 | 3,3 | 3,6 |
| 3 | 40 | 26,35 | 31,33 | 19,17 | 17,14 | 6,9 | 8,9 | 4,4 | 5,3 |
| 6 | 40 | 36,36 | 58,36 | 17,21 | 17,18 | 12,10 | 15,9 | 5,5 | 5,5 |
| 36 | 40 | 36,33 | 49,59 | 33,25 | 23,28 | 10,9 | 13,17 | 6,7 | 7,7 |
| 59 | RT | 37,43 | 60,57 | 11,11 | 12,11 | 14,11 | 15,15 | 0.0 | 5,5 |

TABLE 5
CEFAZOLIN SODIUM COATED WITH EMULPHOR ® EL-719

| | Stor-age Temp. | 10% Solutions Surfactant Conc. (PPM) | | | | 2% Solutions Surfactant Conc. (PPM) | | | |
|---|---|---|---|---|---|---|---|---|---|
| Days | | 0 | 10 | 50 | 100 | 0 | 10 | 50 | 100 |
| 0 | RT | 22,17 | 19,18 | 14,14 | 7,7 | 6,4 | 4,6 | 5,3 | 2,2 |
| 3 | 40° | 51,47 | 39,20 | 23,18 | 8,11 | 13,13 | 13,11 | 6,6 | 6,3 |
| 6 | 40° | — | 47,54 | 20,30 | 10,25 | — | 11,13 | 5,8 | 2,3 |
| 36 | 40° | — | 49,39 | 22,26 | 15,9 | — | 12,10 | 6,6 | 3,2 |

The results reported in the above Tables for the controls indicate that an increase in storage time in the plastic bags yields a proportionate decrease in the clarity (and increase of turbidity) of the reconstituted solutions. The results of the above Table 2 show the presence of lipophlic hydrocarbons on both the powder and in the reconstituted solutions. Therefore, at least part of the increase in turbidity observed in the above Tables 3, 4 and 5 is due to an emulsion of lipophilic substances, which at least in part, are polyethylene monomers or oligomers in the aqueous reconstituted solutions. Indeed, it is expected that the bulk of the lipophilic substances present in the solution are polyethylene monomers and oligomers because the powder was in contact with a pure medium-density polyethylene. Furthermore, the values obtained for the samples where no surfactant was used to coat the cefazolin sodium (controls) shows an increase in turbidity in direct porportion to an increase in storage time.

The values obtained for cefazolin sodium coated with varying concentrations of three different surfactants show that the turbidity decreases with increasing surfactant concentration. As with the results presented in Table 2, the values in Tales 3 through 5 indicate that an increase in the concentration of surfactant results in a decrease in the migration of monomers and oligomers from the plastic bag onto the pharmaceutical powder.

EXPERIMENTAL

The following experimental procedure is provided to further illustrate the process and the composition of the instant invention. The following experimental procedure is not to be construed as limiting of the instant invention.

EXPERIMENT 1

Polysorbate 80, U.S.P. (polyoxyethylene (20) sorbitan monooleate) (360 g) was dissolved isopropyl alcohol (1200 liters). The isopropyl alcohol solution was diluted by the addition of purified water. Sterile cefazolin sodium powder (367 kg) in filter vessels was washed with this alcohol-Polysorbate 80 mixture. The cefazolin sodium-polysorbate 80, U.S.P. composition was then dried under aseptic conditions in a rotating drum under vacuum at 40° C. for 12 hours followed by 50° C. for 24 hours. The heat was supplied with infrared radiation. The dried powder was then milled and blended under aseptic conditions. The sterile coated powder was filled into sterile bulk containers and transferred to the filling area. The sterile powder was then placed in clean, sterile flexible pouches made from a plastic film with a 0.5 mil polyeter outer layer and a 4.0 mil pure medium-density polyethylene inner layer. The plastic pouches had an opening port closed with septum.

We claim:

1. A pharmaceutical composition in a plastic container in which haze tends to form upon re-constitution, said composition consisting essentially of the injectable form of cephalothin, ampicillin, cefamandole, moxalactam, vancomycin, tobramycin or ceftazidime in powder form with a surfactant.

2. A pharmaceutical composition of claim 1, wherein the pharmaceutical compound is the injectable form of cefamandole.

3. A pharmaceutical composition of claim 1, wherein the surfactant is chosen from a group consisting of sucrose dioleate, polyoxyethylene glycol (200) monooleate, sorbitan monolaurate, polyoxyethylene (4) lauryl ether, polyoxyethylene (4) sorbitan monostearate, polyoxyethylene (6) cetyl ether, polyoxyethylene (20) sorbitan monooleate, poly(ethylene glycol)-30 castor oil, poly(ethylene glycol)-40 castor oil, poloxamer 188, polyoxyethylene (20) sorbitan tristearate, polyoxyethylene glycol (400) monooleate, polyoxyethylene glycol (400) monostearate, polyoxyethylene (9) nonyl phenol, polyoxyethylene glycol (400) monolaurate, polyoxyethyelene (4) sorbitan monolaurate, polyoxyethylene (20) oleyl ether, polyoxyethylene (20) sorbitan monopalmitate, polyoxyethylene (20) cetyl ether, polyoxyethylene (40) stearate, sodium oleate, polyoxyethylene (100) stearate and potassium oleate.

4. A pharmaceutical composition of claim 3 wherein the surfactant is polyoxyethylene (20) sorbitan monooleate, poly(ethylene glycol)-40 castor oil, or poloxamer 188.

5. A pharmaceutical composition of claim 2, wherein the surfactant coating is present in the concentration from between about 10 ppm to about 5000 ppm of pharmaceutical compound.

6. A method of claim 2, wherein the surfactant is chosen from the group consisting of sucrose dioleate, polyoxyethylene glycol (200) monooleate, sorbitan monolaurate, polyoxyethylene (4) lauryl ether, polyoxyethylene (4) sorbitan monostearate, polyoxyethylene (6) cetyl ether, polyoxyethylene (20) sorbitan monooleate, poly(ethylene glycol)-30 caster oil, poly(ethylene glycol)-40 caster oil, poloxamer 188, polyoxyethylene (20) sorbitan tristearate, polyoxyethylene glycol (400) monooleate, polyoxyethylene glycol (400) monostearate, polyoxyethylene (9) nonyl phenol, polyoxyethylene glycol (400) monolaurate, polyoxyethylene (4) sorbitan monolaurate, polyoxyethylene (20) oleyl ether, polyoxyethylene (20) sorbitan monopalmitate, polyoxyethylene (20) cetyl ether, polyoxyethylene (40) stearate, sodium oleate, polyoxyethylene (100) stearate and potassium oleate.

7. A method of claim 6, wherein the surfactant is polyoxyethylene (20) sorbitan monooleate, poly(ethylene glycol)-40 castor oil, or poloxamer 188.

8. A method of claim 6, wherein the surfactant is applied to the pharmaceutical compound in a concentration range of between about 10 ppm to about 5000 ppm per amount of pharmaceutical compound present.

9. A method of substantially reducing or eliminating the formation of haze in reconstituted pharmaceutical compositions stored in plastic containers, which comprises the steps of
  (a) applying a solution of surfactant to a water-soluble pharmaceutical compound in powder form wherein said solution is formed with a solvent in which said compound is substantially insoluble;
  (b) drying said pharmaceutical composition; and
  (c) placing said composition in a plastic container in which haze tends to form upon reconstitution;
wherein the pharmaceutical compound is the injectable form of cephalothin, ampicillin, cefamandole, moxalactam, vancomycin, tobramycin or ceftazidime.

10. A method of claim 6, wherein the pharmaceutical compound is the injectable form of cefamandole.

* * * * *